United States Patent
Levine

(10) Patent No.: US 9,662,242 B2
(45) Date of Patent: May 30, 2017

(54) SHOE WITH CUSTOM MOLDED FOOT PLATE AND METHOD OF MAKING

(76) Inventor: Stephen Michael Levine, Miami, FL (US)

( * ) Notice: Subject to any disclaimer, the term of this patent is extended or adjusted under 35 U.S.C. 154(b) by 1723 days.

(21) Appl. No.: 12/190,579

(22) Filed: Aug. 12, 2008

(65) Prior Publication Data

US 2009/0044426 A1    Feb. 19, 2009

Related U.S. Application Data

(60) Provisional application No. 60/955,571, filed on Aug. 13, 2007.

(51) Int. Cl.
   *A61F 5/14*    (2006.01)
   *A43B 7/28*    (2006.01)
   *A43B 17/14*   (2006.01)

(52) U.S. Cl.
   CPC ............ *A61F 5/14* (2013.01); *A43B 7/28* (2013.01); *A43B 17/14* (2013.01)

(58) Field of Classification Search
   CPC ....... A43B 13/181; A43B 13/187; A43B 5/06; A43B 13/20; A43B 13/12; A43B 13/141; A43B 5/00; A43B 7/1425; A43B 7/1445; A43B 7/20; A43B 13/04; A43B 7/2822; A43B 13/14; A43B 13/145; A43B 17/14; A43B 13/183
   USPC .......... 36/88, 93, 43, 44, 71, 154; 12/142 R, 12/142 E, 146 B, 146 M, 142 N
   See application file for complete search history.

(56) References Cited

U.S. PATENT DOCUMENTS

| | | | |
|---|---|---|---|
| 2,417,852 A * | 3/1947 | Zerkle | 36/154 |
| 2,924,849 A * | 2/1960 | Buchman | 425/2 |
| 3,825,017 A * | 7/1974 | Scrima | 36/181 |
| 3,895,405 A * | 7/1975 | Edwards | 12/146 M |
| 4,155,180 A * | 5/1979 | Phillips | 36/129 |
| 4,756,096 A * | 7/1988 | Meyer | 36/44 |
| 5,154,173 A * | 10/1992 | Aultman | 36/154 |
| 5,958,546 A * | 9/1999 | Mardix et al. | 428/71 |
| 6,160,264 A * | 12/2000 | Rebiere | 250/559.22 |
| 6,523,206 B2 | 2/2003 | Royall | |
| 6,745,501 B2 * | 6/2004 | Brown | 36/174 |
| 6,792,699 B2 * | 9/2004 | Long et al. | 36/88 |
| 7,008,386 B2 * | 3/2006 | Alaimo et al. | 600/592 |
| 7,367,074 B1 * | 5/2008 | Bergquist | 12/142 N |
| 2002/0158358 A1 | 10/2002 | Franzene | |
| 2005/0034332 A1 * | 2/2005 | Moschel et al. | 36/101 |
| 2007/0039205 A1 * | 2/2007 | Erb et al. | 36/44 |

FOREIGN PATENT DOCUMENTS

| | | | | |
|---|---|---|---|---|
| CH | EP0458174 A1 * | 11/1991 | | A43B 13/42 |
| DE | EP1314370 B1 * | 5/2003 | | A43B 13/02 |

* cited by examiner

*Primary Examiner* — Clinton T Ostrup
*Assistant Examiner* — Catherine M Ferreira
(74) *Attorney, Agent, or Firm* — Fitzgerald & Isaacson, LLP; David C. Isaacson

(57) ABSTRACT

The present invention is a press molded custom foot plate, a method of making said plate, and a method of making a shoe using said press molded plate wherein said press molded foot plate is formed of a piece of press molded material that is incorporated and used as the insole of a shoe and where an outsole and uppers are attached to the press molded custom foot plate.

15 Claims, 7 Drawing Sheets

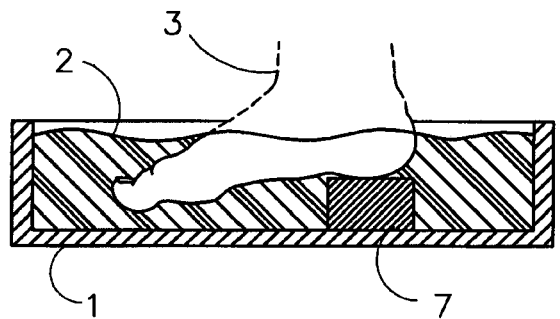
FIG.5
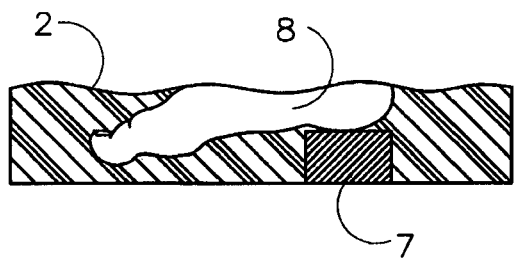
FIG.6
FIG.7
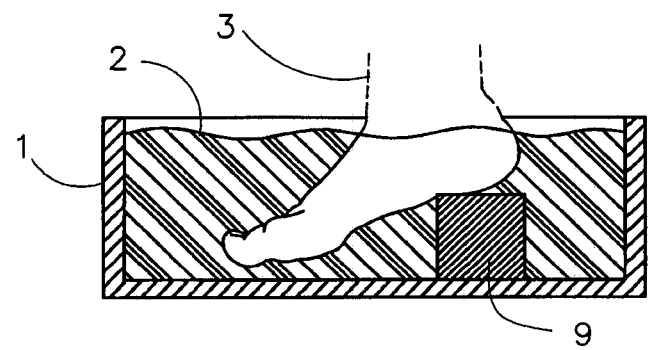
FIG.8
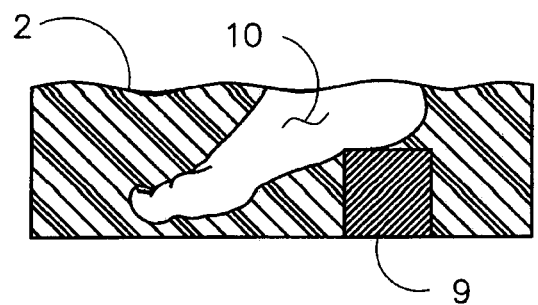

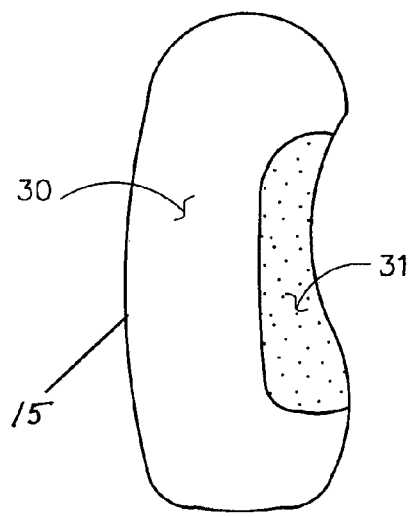 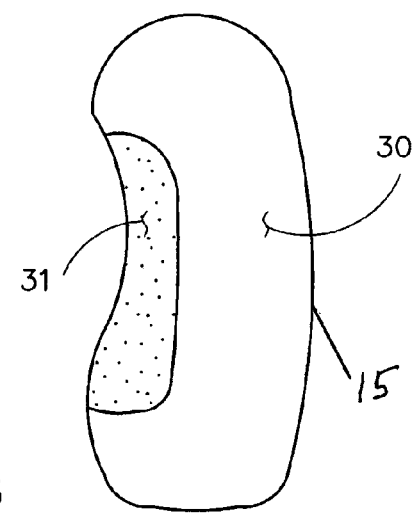
FIG.16
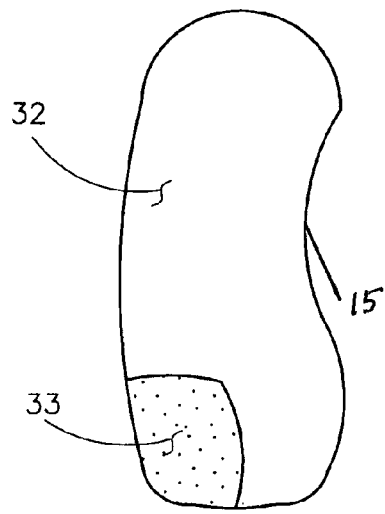 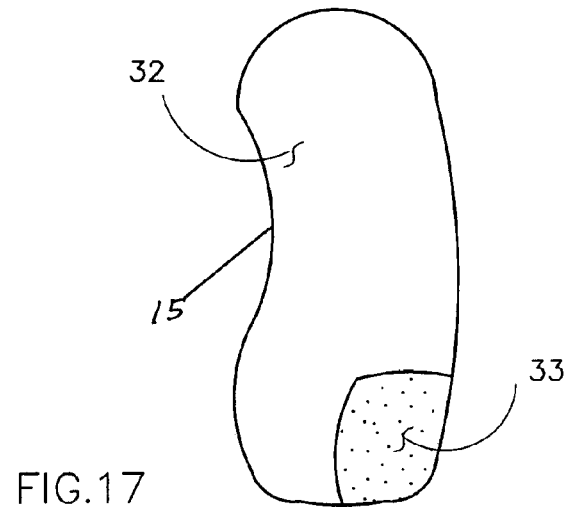
FIG.17

SHOE WITH CUSTOM MOLDED FOOT PLATE AND METHOD OF MAKING

This Application claims benefit of U.S. Provisional Patent Application 60/955,571, filed Aug. 13, 2007, the disclosure of which is incorporated herein by reference in its entirety.

BACKGROUND OF THE INVENTION

Background of the Inventions

There are two types of custom-made foot orthotics in existence, a "custom functional foot orthotic" and a "custom accommodative foot orthotic." A "custom functional foot orthotic" can be described as a shoe insert that is custom designed to realign an individual's foot, so that the foot functions in a more optimal position during weight bearing activities. A "custom accommodative foot orthotic" is a custom made shoe insert that relieves pressure by padding a painful or injured area(s) on the bottom of the foot (e.g. bony prominences and their side effects). When necessary, properties from both types of orthotics can be combined to produce optimal results and address all problematic areas.

The scientific literature documents that a custom foot orthotic, when used with any type of shoe gear, at any heel height, can effectively alleviate foot, ankle, knee and even back pain. Despite their effectiveness, the desire to use such a device is often met with resistance. There are several reasons for this. First, functional orthotics take up a lot of room in the shoes that they are placed in. This often allows the device only to be worn with comfort in a wide, bulky type shoe, such as a sneaker. Second, if a bulky insert is placed in a narrow shoe, shoe deformation can result. This deformation can result in a poorly fitting shoe that may lead to further problems. Third, custom functional foot orthotics generally must be used in closed shoes. Closed shoes allow the orthotics to remain within the shoes and decrease improper positioning of the device. Currently existing orthotics do not work well with open shoes such as sandals or open back shoes.

Custom foot orthotic manufacturers have attempted to develop several methods to resolve these problems. The first was the production of "custom dress orthotics". These devices are thin, less supportive, are often made of only a partial foot length and are, consequently, less effective than the custom functional foot orthotic. They merely act as arch supports when compared to the more bulky, but more effective, custom functional foot orthotic. Because these devices are manufactured of only a partial foot length, they often move around within the shoe and are not held properly against the bottom of the foot. This leads to discomfort. More specifically, women commonly complain of pain in the balls of their feet when weight bearing in high heeled shoes. A dress orthotic cannot adequately alleviate this complaint because a downward sliding motion of the dress orthotic occurs. This sliding does not allow for the dress orthotic to re-distribute some of the body weight from the ball of the foot to the heel. Also of importance is that custom dress orthotics are manufactured so that they best function in shoes with a predetermined heel height. As the heel height of a shoe increases, the actual foot arch height is also increased. Consequently, a custom dress orthotic that is manufactured for a shoe of a low heel height will result in a custom foot orthotic with a low arch height. If this device is then transferred to and used in a shoe of a higher heel height, the arch area of the custom foot orthotic will not adequately support the newly heightened position of the foot arch. On the contrary, if a custom foot orthotic was manufactured for use in a shoe with a high heel height and if it is transferred to a low arch shoe, the arch height of the orthotic would be too high for the newly positioned arch height of the foot.

Second, manufacturers have suggested that functional foot orthotics can be made to fit into specific brands of pre-made shoes that have thick, removable insoles. An example of these shoes would be the brand marketed under the name "Naot" a Trademark of NA'ALE NAOT (1994) LTD. "Naot" produces various types of shoes including sandals, casual dress shoes, and sportswear shoes. Even though using this type of shoe does provide for a slightly greater variety of shoe selection, significant shortcomings are still noted. This type of shoe was not designed for use with a custom foot orthotic. They were designed to be used with a thick, cork, insole that the shoe is manufactured with. As a consequence, a functional foot orthotic manufactured for this type of shoe often has to be modified so that the length, width and height of the device is equal to that of the non-functional, thick insole that came with the shoe. This compromise can result in a custom functional foot orthotic that does not function optimally. Furthermore, since these are manufactured to accommodate the pre-made bulky insole, the shoes themselves are often bulky in the sole region and not aesthetically appealing. Dress type shoes are generally not made by these companies for this reason.

In order to fully understand the present invention, the three basic components of a conventional shoe must first be described. A shoe basically consists of an upper, an insole, and an outsole. An upper is the portion of a shoe that covers the foot. An insole consists of a layer of material that sits inside the shoe and creates a layer between the sole and the wearer's foot. If removable, this is the portion of the shoe that is replaced by the custom functional foot orthotic. The outsole is the exposed portion of the sole that is in contact with the ground.

BRIEF SUMMARY OF THE INVENTION

As discussed in the background of the invention section, a custom functional foot orthotic that is placed over, or replaces the insole of a non-custom made shoe often results in resistance to using the device because of a variety of reasons that include but are not limited to: 1. taking up too much room in a shoe; 2. causing shoe deformation; 3. Generally requiring the use of closed shoes; 4. sliding of the "custom dress orthotics" within the shoe; 5. Not functioning optimally when switched to a shoe of a different heel height; 6. Pre-made, Naot type shoes being too bulky and not aesthetically appealing for dress; 7. Having to compromise function of the orthotic so that it can fit in a specific shoe.

The present inventions, which includes the presented device (the shoe), as well as the method for producing the device, addresses and resolves all of the above issues, regarding the resistance to using custom functional foot orthotics, by producing an entire "custom functional shoe". The key factor that distinguishes this shoe from a conventional shoe is a newly invented custom molded foot plate ("the custom foot plate"). The "custom foot plate" is a solid unit that consists of two components, a custom functional foot orthotic and a "forefoot extension". In essence, the "custom foot plate" is a device that extends the full length of the shoe. This invention provides a full length platform to which the basic components of the conventional shoe can be attached, those being the upper, insole and outsole. The "custom foot plate" is the insole and is positioned above the out sole portion of the shoe.

With the advent of the "custom functional shoe", which contains the "custom foot plate", a custom functional foot orthotic is no longer placed in the shoe. The custom functional orthotic is now incorporated into the shoe. This eliminates the need to place any space occupying object within the shoe. As a result, shoe deformation that occurs with the use of custom functional foot orthotics will no longer occur. Because the custom functional foot orthotic is no longer a separate entity from the shoe, it can no longer cause discomfort from sliding around in the shoe. Regarding high heeled shoes, weight can now be adequately redistributed from the ball of the foot to the heel. As a result, the "custom functional shoe" alleviates pain in the ball of the foot that is commonly present in wearer's of conventional high heeled shoes. Moreover, any type of shoe can be constructed with this method, including strapped shoes, open shoes, closed shoes etc. Because the functional foot plate is made specifically for the heel height of the shoe that it is incorporated in, the custom functional foot orthotic portion will always function optimally. The foot plate is thin, because it is press molded, thus shoes made with this device do not have to be bulky and therefore are more aesthetically appealing. The functional portion of the orthotic no longer has to be altered so that it fits into a shoe.

In one embodiment the invention is a custom shoe sole having a press molded foot plate formed from a positive mold of a foot. The press molded foot plate extends substantially the length of said foot.

Preferably, the custom press molded foot plate is formed of a heat moldable material. Suitable materials may include, but would not be limited to polypropylene, polyethylene, acrylic, graphite, fiberglass, carbon fiber material, a composite material Ethylene-vinyl acetate (EVA), polyethylene, polyethylene foams, closed cell cross-linked polyethylene foam, cork, or combinations thereof.

In a preferred embodiment, the custom press molded foot plate has a uniform thickness.

The present invention also encompasses a shoe with a custom insole having:
a. a press molded foot plate;
b. uppers;
c. an outer sole; and
d. optionally, a heel.

The shoe has a press molded foot plate formed of a heat moldable material.

The shoe can have uppers positioned to avoid pressure on parts of a foot expressing podiatric pathology or anomaly.

The shoe can have a heel that is relatively flat in relation to an outer sole of said shoe or a low to high heel up to about 4-5 inches.

The shoe has uppers and an outsole attached to the molded foot plate. The press molded foot plate is the insole of said shoe.

The shoe may have a heel. If a heel is desired, it is also attached to the press molded foot plate.

Also contemplated is a method of making a shoe having the steps of:
a. forming a negative cast of a foot;
b. casting a positive mold from said negative cast;
c. adding a fore foot extension forming structure to said positive mold;
d. placing said positive mold on a vacuum forming base plate;
e. covering said positive mold with a moldable material;
f. placing a vacuum mold head over said positive mold with said moldable material;
g. press molding said moldable material to form a custom foot plate;
h. removing said custom foot plate from said positive mold;
i. cutting said custom foot plate to a desired shape; and
j. attaching uppers and an outsole to said custom foot plate;
k. wherein said custom foot plate is the insole of said shoe.

In one embodiment the present invention may be described as follows:
1. Negative Impression and Positive Mold Formation:

A desired shoe style and heel height are first selected. If using plaster of paris rolls, or fiberglass rolls as casting material, the foot is held at the same heel height as the selected shoe. This is accomplished with a block (heel riser), or any other appropriate device, which is placed under the heel region of the foot. The casting material is applied to the foot as a slipper type cast. The foot and leg are then placed into the same position they would be in as if statically standing in the selected shoe. The casting material is allowed to set while the foot and leg are held in the position that was described. The formed negative cast mold is then removed from the foot. Liquid molding material, such as plaster of paris is poured into the negative mold and allowed to set. This will form the positive mold. Once set, the negative cast mold is separated from the positive cast mold. Note that any of the modifications used in the art of foot orthotic manufacturing can be applied to biomechanically correct the negative or positive molds.

2. Method of Adding Described "Forefoot Extension":

A pre-formed fore foot extension casting apparatus or mold is then attached to the front of the positive mold or casting. Note that this apparatus should resemble the pattern and size of the forefoot region of the sole of the selected shoe. The positive mold is then placed in the same position that the foot was held in during production of the negative cast before pouring the mold. Hence, the same heel riser is used to elevate the heel of the positive mold. The mold is poured and allowed to set while maintained in the described position. This addition, the "forefoot extension", elongates the orthotic portion of the foot plate so that it is the entire length of the shoe sole. Furthermore, the "forefoot extension" will allow for the forefoot, mainly the ball and toe portion of the foot, to rest on a flat surface when standing. Note that any functional or accommodative modifications can also be added to the "forefoot extension".

3. Vacuum Pressing Positive Mold with Added Forefoot Extension to Manufacture the "Custom Foot Plate":

The positive mold with added "forefoot extension" is then placed in a vacuum press machine. A sheet of material, such as polypropylene is heated to the temperature which is recommended, by the supply company, for molding. The recommended degree of temperature is material specific and is common knowledge in the art of orthotic making. The heated sheet of material is then placed over the positive mold and vacuum pressed. When set, the newly formed "custom foot plate" (pressed polypropylene in this example) is separated from the positive casting.

4. Method of Trimming Excess Material from the "Custom Foot Plate" to Fit Selected Shoe:

The excess material is cut from the "custom foot plate'" edges. A grinding wheel is then used to form the "custom foot plate" into the desired shape. Note that a pre-made template, which resembles the shape of a tracing of the sole of the selected shoe, can be temporarily adhered to the foot plate and allow for rapid grinding of the "custom foot plate" into the desired shape. Note that the described template would have to be constructed of a material that does not grind as easily as the material that the foot plate is made of (e.g. metal sheet).

5. Shoe Assembly:

Pre-fabricated or customized uppers, insoles, soles, and heels will be attached to the "custom foot plate". The "custom foot plate" is incorporated into the shoe as an insole. It may be held between the an upper cushioning material and the sole portion of the shoe. The thin layer of cushioning that overlies the custom molded foot plate is preferably non-slip, is attached to the top part (part that sits against the plantar aspect of the foot) of the foot plate. The uppers (any type . . . straps, enclosed etc.) are adhered to the "custom foot plate". Note that the placement of the uppers can be modified so that they do not rest against painful areas, e.g. straps can be placed to avoid pushing on a bunion. Note that the desired tightness of the uppers can be pre-determined by trial measurements made prior to shoe construction. This can be accomplished placing a template that resembles the sole of the selected shoe, against the foot. Upper sole placement and tautness can be pre-determined in this way. The heel is then attached to the "custom foot plate". The outsole material is then adhered to the under surface (the part that faces the ground) of the "custom foot plate", and if desired, to the heel as well. The final product is then completed.

Any podiatric pathologies or anomalies which may be treated or ameliorated with custom functional or accommodating foot orthotics may be incorporated into the custom molded foot plate of the present invention.

BRIEF DESCRIPTION OF THE DRAWINGS

FIG. 5 is a side cut away of a foot in a mold with the heel being placed atop a low heel riser.

FIG. 6 is a side cut away view of the mold after a foot is removed, with a low heel riser remaining in the mold.

FIG. 7 is a side cutaway view of a foot in a mold with the heel being placed atop a high heel riser.

FIG. 8 is a cut away view of the mold after the foot is removed, with a high heel riser remaining in the mold.

FIG. 16 is a top view of the molded foot plate having regions of different densities.

FIG. 17 is a top view of the molded foot plate having regions of different densities.

DETAILED DESCRIPTION OF THE PREFERRED EMBODIMENTS

Figure 1:
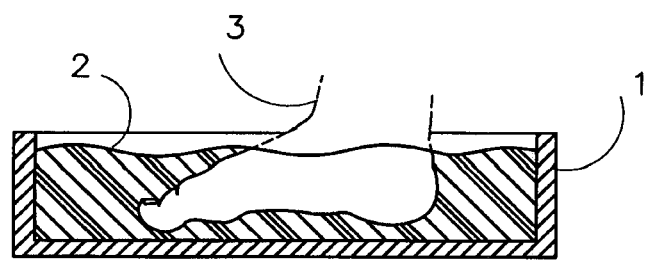
FIG. 1 is side cut away of a foot in a mold.

The present invention relates to the formation of a custom footplate and subsequent incorporation of the custom footplate into the fabrication of a shoe.

A casting mold 1 is filled with casting material 2 that will form an impression when a foot 3 is placed therein. When foot 3 is removed, foot cast cavity 4 in the shape of foot 3 is formed.

A casting material 5 is placed into cavity 4 to form a positive mold 6.

A casting with a low heel is formed, as shown in FIG. 5, by placing a low heel riser 7 in casting mold 1 before foot 3 is inserted therein. Cavity 8 is for casting a positive mold to be used in a low heel shoe. Typically, a low heel shoe has a height of about 1½ to 2 inches and lower.

A casting with a high heel is formed, as shown in FIG. 7, by placing a high heel riser 9 in casting mold 1 before foot 3 is inserted therein. Cavity 10 is for casting a positive mold to be used in a high heel shoe. Typically, a high heel shoe has a height of about 1½ to 2 inches and higher.

Negative castings, as are commonly known are used to form positive molds used in fabricating the custom molded foot plate of the present invention.

Although positive mold 6 is referenced herein, it is contemplated that castings formed from low heel cavity 8 or high heel cavity 10 may be used similarly.

Figure 9:
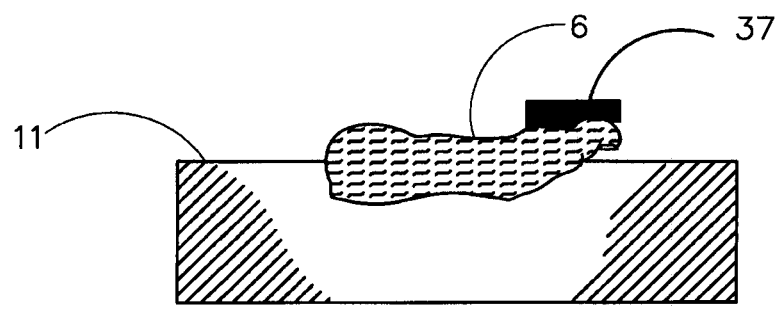
FIG. 9 is a side cut away of a casting positioned on a vacuum mold.
Figure 10:
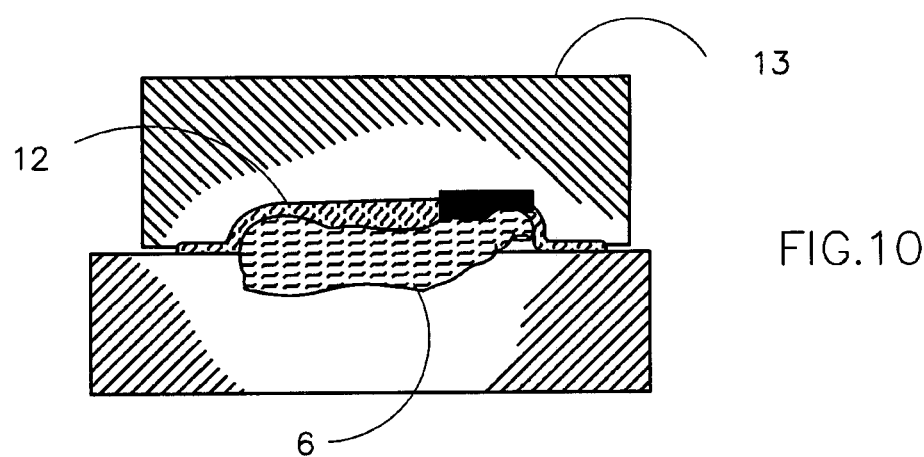
FIG. 10 is a side cut away of vacuum mold with shoe base plate material on a casting.
Figure 11:
FIG. 11 is a side cut away of shoe base plate material formed around a casting.
Figure 12:
FIG. 12 is a side cut away of the shoe base plate material formed around a casting that has been trimmed.
Figure 13:
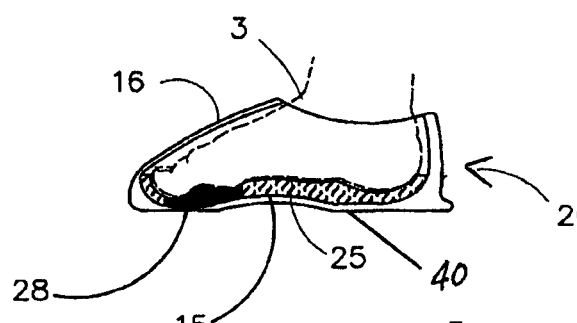
FIG. 13 is a side cut away of the shoe base plate material with shoe uppers in place.
Figure 14:
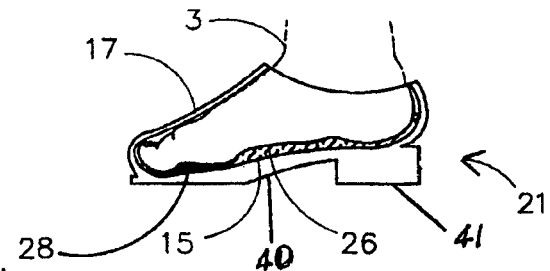
FIG. 14 is a side cut away of a low heel shoe having base plate material with shoe uppers in place.
Figure 15:
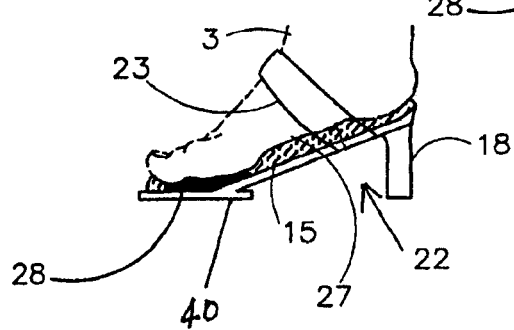
FIG. 15 is a side cut away of a high heel shoe having base plate material with straps in place.

Referring to FIGS. 9 and 10, positive mold 6 is placed on a vacuum forming mold base 11. Moldable footplate material 12, typically provided as a planer sheet, is placed over positive mold 6. Positive mold 6 is then covered with vacuum mold head 13. Material 12 is press molded to form unfinished foot plate 14 corresponding in shape to positive mold 6. The process of press molding is carried out by those procedures as are commonly known in the art. Vacuum mold head 13 is removed and the resultant unfinished foot plate 14 formed from the press molding of material 12 is removed. Unfinished foot plate 14 is then trimmed on all sides to form custom molded foot plate 15. Custom molded foot plate 15 is of size and shape, after trimming, to be incorporated into the fabrication of a shoe. Unlike orthotics, which are placed in a shoe on top of an existing inner shoe sole, custom molded foot plate 15 is the insole of the shoe. Shoe uppers, outsole 40, and any desired heel are constructed and arranged such that they attach directly to custom molded foot plate 15 by any acceptable means. Attachment of uppers 16 and outer sole 40 to custom molded foot plate 15 may include but would not be limited to, adhesive, sewing or stitching and any other means as commonly known which would securely attach uppers and outer sole 40 to custom molded foot plate 15. As depicted in FIGS. 13, 14, and 15, each shoe 20, 21, and 22 has a custom molded foot plate 15 fabricated as described herein.

Uppers 16 for flat shoe 20, uppers 17 for low heel height shoe 21, or uppers 23 for high heel shoe 22, are attached to custom molded foot plate 15 to complete the shoe structure. Uppers may be attached to custom molded foot plate 15 of any shoe at any desired heel height.

As discussed above, moldable footplate material 12 is positioned on positive mold 6. Moldable footplate material 12 is heated if needed. Positive mold 6 is positioned between a vacuum forming mold base 11 and a vacuum mold head 13. Vacuum forming mold base 11 and a vacuum mold head 13 are brought together to form unfinished foot plate 14 that is produced by press molding as is commonly known. The present invention uses a press molding process to form custom molded foot plate 15, as an advantageous technique to use in the formation of custom molded foot plate 15. Press molding, unlike previous techniques such as, but not limited to injection molding, provides the advantage that press molding is simpler, less expensive, and allows the sole thickness and uniformity may be more tightly controlled. Press molded articles typically maintain a uniform thickness relative to the thickness of the substrate subjected to the press molding process. The control of thickness and uniformity is desirable when forming custom molded foot plate 15 such that custom molded foot plate 15 does not become prohibitively bulky or heavy.

The custom molded foot plate 15 of the present invention may be formed of any suitable material. Suitable materials for standard shoes may include but would not be limited to, polypropylene, polyethylene, acrylic, graphite, fiberglass, carbon fiber material, a composite material, or combinations thereof. Suitable materials are any materials that are able to be used in the press molding process. Said materials should be thin, durable, stiff, and heat moldable. In a preferred embodiment, they would be covered with a thin layer of cushioning, on either or both sides, such as foam and the like as is commonly done in the manufacture of shoes.

For athletic shoes to be constructed, custom molded foot plate 15 may be made of a material providing a greater cushioning to a user. Examples of materials suitable for a custom molded foot plate in an athletic shoe would include, but would not be limited to, polypropylene, polyethylene, acrylic, graphite, fiberglass, carbon fiber material, a composite material, Ethylene-vinyl acetate (EVA), Nickelplast™ (a combination of ethylene vinyl acetate and polyethylene, available from Alimed, Inc., Dedham, Mass.), polyethylene foams, PLASTAZOTE® (Closed cell crosslinked polyethylene foam, available from Zotefoams, PLC, Surrey, England), cork, or combinations thereof.

The different suitable materials for custom molded foot plate 15 in both standard and athletic shoes, can be used by themselves or as a combination. For example, a standard shoe custom molded foot plate 15 may be formed of a combination of polypropylene, polyethylene, and acrylic. An example of a custom molded foot plate 15 for an athletic shoe may include a combination of EVA and polyethylene foams. These examples are for illustrative purposes only and not intended to limit the combinations of materials available to for the custom molded foot plate 15 of the present invention.

Alternatively, any combination of any suitable moldable materials may be used to produce custom molded foot plate 15 of the present invention. It is known that many of the suitable materials for forming custom molded foot plate 15 of the present invention have different densities. A custom molded foot plate 15 may be constructed and arranged such that custom molded foot plate 15 prevents or inhibits undesirable motions. For example, as shown in FIG. 16, if a person has a flat foot, a denser material 31 can be placed on the medial portion of custom molded foot plate 15, and a less dense material 30 can be placed on the lateral portion of custom molded foot plate 15. Placement of materials having different densities in custom molded foot plate 15 would prevent the foot from flattening in an undesired manner. Additionally, denser material 33 may be placed by the posterior lateral heel region, and less dense material 32 is placed along the remaining portion of custom molded foot plate 15, as shown in FIG. 17. The placement of more dense and less dense materials is incorporated into custom molded foot plate 15 during the press molding process. This would encompass using two or more materials covering positive mold 6 prior to press molding custom molded foot plate 15. The general concept of constructing and arranging a sole with different densities is already used in various running shoes to prevent foot pronation. The shoes with soles of varying densities to control foot pronation are called motion controlled shoes. The custom molded foot plate 15 of the present invention has further improved on motion controlled shoes by providing a custom molded foot plate 15 that can be customized in any manner used to customize foot orthotics. The custom molded foot plate 15 of the present invention is used to treat any other foot pathology that would benefit from the use of a prescription foot orthotic.

Figure 2:
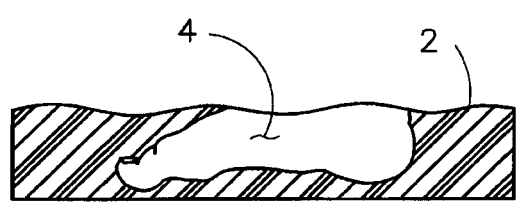
FIG. 2 is a side cut away of the mold after a foot is removed.
Figure 3:
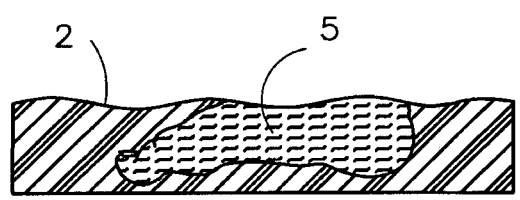
FIG. 3 is a side cut away of the mold removed from a casting.
Figure 4:
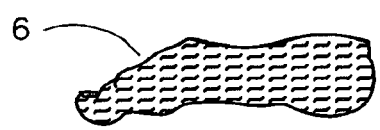
FIG. 4 is a side cut away of the casting removed from the mold.

In a preferred embodiment, a negative mold may be formed by conventional molding techniques; however, the method of forming the negative mold is not limited to these techniques, and other techniques may be employed. In one manner of forming a negative mold, a cavity 4 is formed by stepping into casting material 2, as depicted in FIGS. 1-2. The foot is pushed into moldable casting material and leaves an indentation.

A negative mold may be formed by plaster or fiberglass casting in which the foot is wrapped in a plaster or fiberglass bandage. The bandage is allowed to dry and harden forming a negative cast. Liquid plaster or any acceptable casting media, is poured into the negative cast to form a positive cast or positive mold. A custom molded foot plate 15 is then formed from this positive cast.

Laser imaging, as is commonly know in the art, may also be used to create custom foot molds for use in fabricating articles of the present invention. TracerCad® (The Ohio Willow Wood Co., Mt Sterling, Ohio) and Foot Fax-SL® (Amfit, Inc., Vancouver, Wash.) are two examples of commercially available laser scanners that can scan the foot. The foot is scanned, the scan is transmitted to a milling machine and the milling machine cuts a positive mold from a solid. The solid may be wood, plastic, or any material that may be milled by milling machines as are commonly known.

Positive mold 6 may be cast in a manner for producing a custom molded foot plate 15 that will be used in a shoe without an elevated heel. If desired, a negative mold 8 may be cast using a low heel riser 7, or negative mold 10 may be cast using a high heel riser 9. In using either a low heel riser 7, or a high heel riser 9, negative mold is cavity 8 or 10 respectively, is cast such that the arch height of custom molded foot plate 15 is correctly positioned in relation to the desired heel height. It is important to cast negative mold 8 or 10 at the heel height that will ultimately be used in the finished shoe because the arch height of a foot is increased as the heel height increases. Positive mold 6 has a plate 37, which will impart fore foot extension 28 on the custom molded foot plate 15 after press molding.

The fore foot extension 28 is formed as described in the summary of the invention and provides a flat surface for the foot to rest upon and completes of the full length and shape of the custom molded foot plate 15. The fore foot extension 28 is part of a unitary structure that is integral with the custom molded foot plate 15 of the present invention.

A mold will most closely conform to the sole of the foot when the mold is taken at the heel height that will be used. A mold that is taken of a foot without a heel will create a cast that has an inaccurate arch height when incorporated into a shoe with a heel. Conversely, a mold that is cast from a foot at a heel height higher than will be used will create an arch height that is ineffectively high. There is a need for casting a mold at the same height in which heels will be used. As the heel is raised off the ground, the height of the arch increases proportionally. It is imperative that the casting occur at the desired heel height such that the sole of the foot has continual contact with the upper portion of custom molded foot plate 15. When negative mold (any of cavities 4, 8, or 10) is cast at the desired height of a finished shoe, the negative mold will be used to create custom molded foot plate 15 with a more secure and contoured fit. The custom molded foot plate 15 formed from a cast with a heel riser equal to that of a heel in which the custom molded foot plate 15 will be used forms an insole that more closely conforms, and preferably exactly conforms, to the shape of the foot that made the casting.

A finished shoe has integral custom molded foot plate 15 with uppers 16, 17 or 23, heels 41 or 18, and outsole 40 that are directly attached to said custom molded foot plate 15 to form a custom shoe. Unlike conventional orthotics, the custom molded foot plate of the present invention is not placed on top of a shoe insole, the custom molded foot plate 15 is the entire insole.

Figure 18:
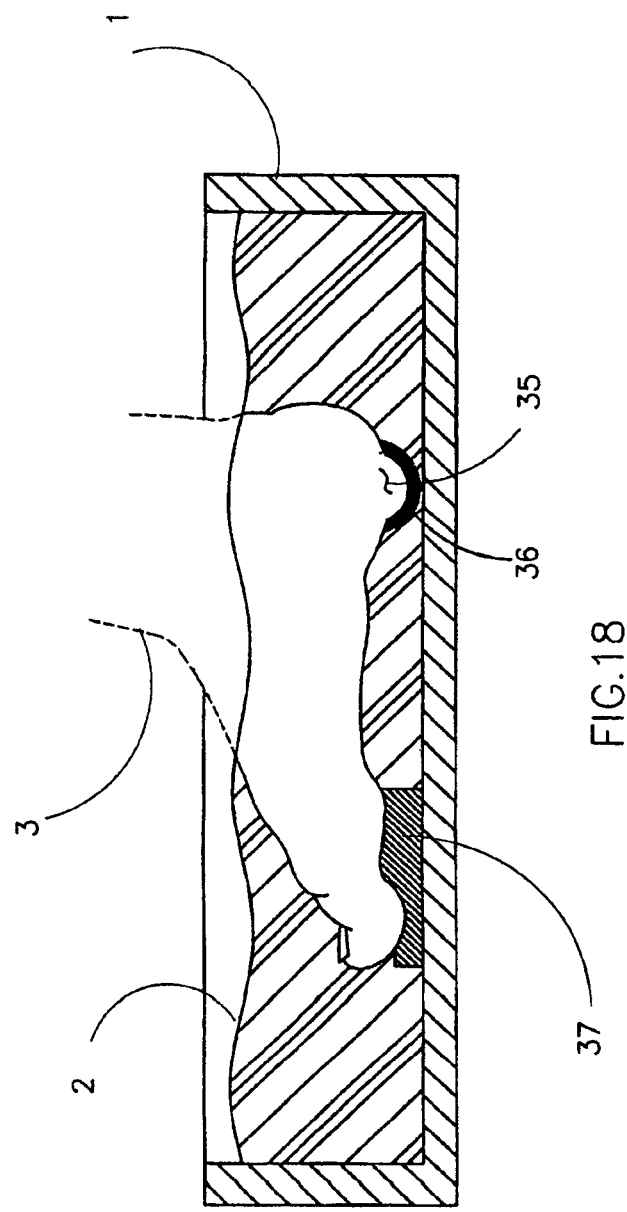
FIG. 18 is a side cut away of a foot having a bony prominence being cast.

The shoes of the present invention are custom made. They can be constructed and arranged to fit any foot type or deformity. For example, women with bunion deformities often have difficulty finding shoes that do not have a strap that sits over the bunion (a strap over a bunion may cause pain to the wearer). Strap 23 in shoes of the present invention can be positioned to avoid the bunion. Additionally, any other bony prominences in the foot can be accommodated in the custom molded foot plate 15 and in any other parts of the shoe in which accommodation would be beneficial to the wearer. Apertures can be placed in custom molded foot plate 15, as shown in FIG. 18. A bony prominence 35 may be covered with a cover 36 that will impart an aperture into negative mold (any of cavities 4, 8, or 10) that will be accommodated in custom molded foot plate 15. The cover may be any suitable cover and may include, but would not be limited to a bandage or additional casting material placed over bony prominence 35. Custom molded foot plate 15 constructed and arranged to accommodate bony prominences will ultimately result in a custom molded foot plate and ultimately finished shoe which can offload painful bony prominences on the bottom of feet. The shoe and incorporated custom molded foot plate 15 will conform to any perturbance of the foot and would not be limited to accommodating bony prominences.

In another embodiment, a physical aperture may be formed on the custom molded foot plate 15 by capturing the prominence on either the positive mold 6 or negative mold. This can be done by forming either a prominence on the positive mold before molding or an indentation on the negative mold at the desired location.

Any modifications that are commonly used in the fabrication of conventional orthotics may be used as modification in custom molded foot plate 15 of the present invention.

The shoes of the present invention can be made as wide or narrow as needed. This includes custom fit uppers 16, 17 or 23, which can be constructed as loose or tight as needed to accommodate the needs of the wearer.

With regard to high heeled shoes, as shown in FIG. 15, since the custom molded foot plate 15 is custom cast and formed at a height equal to high heel 18, a greater surface area of the sole of the foot will be in contact with custom molded foot plate 15 in comparison to conventional high heel shoes. The casting of the custom molded foot plate 15 at the height of the heels to be used forms a casting with the arch height being properly positioned for the specific heel height. FIG. 13 has interface 25 showing the sole and arch of the foot in continual and substantially or complete contact with custom molded foot plate 15 when used in flat shoe 20. FIG. 14 has interface 26 showing the sole and arch of the foot in continual and substantially or complete contact with custom molded foot plate 15 when used in low heel 41 of low heel shoe 21. FIG. 15 has interface 27 showing the sole and arch of the foot in continual and substantially or complete contact with custom molded foot plate 15 when used in high heel 18 of high heel shoe 22. Custom molded foot plate 15 used in high heeled shoes will distribute the gravitational force more evenly throughout the sole of the foot and the shoe resulting in a significantly decrease in the amount of pain and/or pressure that people experience in the ball of their foot while wearing high heeled shoes.

Figure 19:
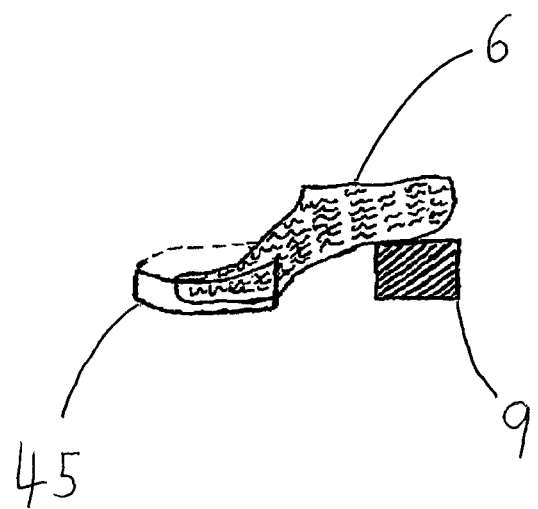
FIG. 19 is a side cut away of the casting with the fore foot extension mold positioned by the fore foot.

FIG. 19 shows positive mold 6 with heel riser 9. Fore foot extension mold 45 is filled with casting material 2. Fore foot extension mold 45 has an inner cavity to receive casting material 2 and may be shaped to conform to the type of shoe desired e.g. square toe, pointed, rounded, etc. After casting material 2 is hardened, forefoot extension mold 45 is removed and forms plate 37. Plate 37 will impart fore foot extension 28 on the custom molded foot plate 15 after press molding. As stated above, fore foot extension 28 is unitary, contiguous and integral with molded foot plate 15. Although FIG. 19 depicts use with heel riser 9, it is contemplated that extension mold 45 may be used with any heel riser or without a heel riser. Fore foot extension mold 45 should be positioned and filled with casting material 2 while positive mold 6 is at the heel height desired in the completed shoe. Positive mold 6 should remain at the desired heel height of the finished shoe until casting material 2 inside fore foot extension mold 45 has hardened.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A custom shoe corresponding to the shape of a foot at a heel height of the shoe comprising:
    a custom molded foot plate formed from a positive mold of the foot made at the heel height of the shoe, said foot plate having a uniform thickness and extending substantially an entire length of the foot, and said foot plate having a heel portion, an arch portion and a toe portion, wherein when the toe portion of the foot plate is placed on a substantially flat surface the heel portion of the foot plate is at the heel height of the shoe;
    an outsole attached to said foot plate;
    a heel being of a height for establishing the heel height of the shoe, said heel attached to said outsole at said heel portion; and
    at least one upper attached to said foot plate.

2. A custom shoe as in claim 1, wherein said heel is at an elevated height.

3. The custom shoe as in claim 1 wherein said foot plate is formed of a heat moldable material.

4. The custom shoe sole of claim 3 wherein said heat moldable material is selected from the group consisting of polypropylene, polyethylene, acrylic, graphite, fiberglass, carbon fiber material, Ethylene-vinyl acetate (EVA), combinations of ethylene vinyl acetate and polyethylene, polyethylene foams, closed cell cross-linked polyethylene foam, cork, and mixtures thereof.

5. A custom shoe corresponding to the shape of a foot at a heel height of the shoe comprising:
   a custom molded foot plate formed from a positive mold of the foot made at the heel height of the shoe, said foot plate having a uniform thickness and extending substantially an entire length of the foot, and said foot plate having a heel portion, an arch portion and a toe portion, wherein when the toe portion of the foot plate is placed on a substantially flat surface the heel portion of the foot plate is at the heel height of the shoe; and
   an outsole attached to said foot plate.

6. A custom shoe corresponding to the shape of a foot at a heel height of the shoe as claimed in claim 5 including:
   a heel being of a height for establishing the heel height of the shoe, said heel attached to said outsole at said heel portion; and
   at least one upper attached to said foot plate.

7. A custom shoe as in claim 6, wherein said heel is at an elevated height.

8. The custom shoe as in claim 5 wherein said foot plate is formed of a heat moldable material.

9. The custom shoe sole of claim 8 wherein said heat moldable material is selected from the group consisting of polypropylene, polyethylene, acrylic, graphite, fiberglass, carbon fiber material, Ethylene-vinyl acetate (EVA), combinations of ethylene vinyl acetate and polyethylene, polyethylene foams, closed cell cross-linked polyethylene foam, cork, and mixtures thereof.

10. The custom shoe as in claim 5 wherein said foot plate is formed of a heat moldable material.

11. The custom shoe sole of claim 10 wherein said heat moldable material is selected from the group consisting of polypropylene, polyethylene, acrylic, graphite, fiberglass, carbon fiber material, Ethylene-vinyl acetate (EVA), combinations of ethylene vinyl acetate and polyethylene, polyethylene foams, closed cell cross-linked polyethylene foam, cork, and mixtures thereof.

12. The custom shoe as in claim 1, wherein the foot plate comprises:
   a top surface having a contour; and
   a bottom surface having a contour, wherein the contour of the bottom surface of the foot plate follows the contour of the top surface of the foot plate.

13. The custom shoe as in claim 1, wherein the thickness of the foot plate is uniform substantially along the length of the foot plate passing through the arch of the foot plate.

14. The custom shoe as in claim 5, wherein the foot plate comprises:
   a top surface having a contour; and
   a bottom surface having a contour, wherein the contour of the bottom surface of the foot plate follows the contour of the top surface of the foot plate.

15. The custom shoe as in claim 5, wherein the thickness of the foot plate is uniform substantially along the length of the foot plate passing through the arch of the foot plate.

\* \* \* \* \*